(12) United States Patent
Raghavan et al.

(10) Patent No.: US 6,331,638 B1
(45) Date of Patent: Dec. 18, 2001

(54) PROCESS FOR THE PREPARATION OF 1,8-DISUBSTITUTED-1,3,4,9-TETRAHYDROPYRANO (3,4-B)-INDOLE-1-ACETIC ACID ESTERS

(75) Inventors: B. Vijay Raghavan, New Delhi; K. V. Ramana, Gurgaon; Brij Khera, New Delhi; Naresh Kumar, Gurgaon, all of (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/412,455

(22) Filed: Oct. 4, 1999

(51) Int. Cl.$^7$ ................................................ C07D 491/052

(52) U.S. Cl. .............................................................. 548/432

(58) Field of Search ............................................. 548/432

(56) References Cited

U.S. PATENT DOCUMENTS

| | | | |
|---|---|---|---|
| 3,939,178 | 2/1976 | Demerson et al. | 260/326.28 |
| 4,012,417 | 3/1977 | Demerson et al. | 260/326 |
| 4,309,348 | 1/1982 | Asselin et al. | 260/326.28 |
| 4,585,877 | 4/1986 | Demerson et al. | 548/432 |

OTHER PUBLICATIONS

Costa P R R et al: "Asymmetric Friedel–Crafts Reaction Mediated by New Chiral Auxillaries Derived from (1S)–(@?)–beta–Pinene: Enantioselective Synthesis of (@?)–8–Norethyl, 1@?–Normethy Etodolac", Tetrahedron Letters, NL, Elsevier Science Publishers, Amsterdam, vol. 38, No. 40, Oct. 6, 1997 (Oct. 6, 1997), pp. 7021–7024.

*Primary Examiner*—Floyd D. Higel
*Assistant Examiner*—Ebenezer Sackey
(74) *Attorney, Agent, or Firm*—Jayadeep R. Deshmukh, Esq.

(57) ABSTRACT

A process for the preparation of the esters of 1,8-disubstituted-1,3,4,9-tetrahydropyrano (3,4-b)-indole-1-acetic acid is delineated.

18 Claims, No Drawings

PROCESS FOR THE PREPARATION OF 1,8-DISUBSTITUTED-1,3,4,9-TETRAHYDROPYRANO (3,4-B)-INDOLE-1-ACETIC ACID ESTERS

FIELD OF THE INVENTION

This invention relates to a process for the preparation of the esters of 1,8-disubstituted-1,3,4,9-tetrahydropyrano (3,4-b)-indole-1-acetic acid.

BACKGROUND OF THE INVENTION

The esters of the present invention are used as intermediates for the preparation of the corresponding 1,8-dialkyl-1-3,4,9-tetrahydropyrano (3,4-b)-indole-1-acetic acids, which include etodolac, an anti-inflammatory and analgesic compound reported first by Demerson et al., U.S. Pat. No. 3,939,178.

Throughout, preparation of these esters has been previously described in U.S. Pat. Nos. 3,939,178; 4,012,417; 4,585,877; and several related patents. These esters are prepared from the corresponding 7-substituted tryptophol and alkyl propionylacetate. U.S. Pat. Nos. 3,939,178 and 4,012,417 disclose reaction of substituted tryptophols with keto ester to produce pyrano (3,4-b) indoles. Suitable solvents described are benzene, toluene, diethyl ether, dioxan, tetrahydrofuran, methylene dichloride, carbon tetrachloride and the like. Benzene and tetrahydrofuran are the preferred solvents.

Suitable acid catalysts which may be used for this condensation are the type of catalysts used in Fischer Indole Synthesis and include p-toluenesulfonic acid, phosphorus pentoxide, boron trifluoride, zinc chloride, hydrochloric acid and sulfuric acid and the like. Preferred catalysts being p-toluenesulfonic acid, boron trifluride and phosphorus pentoxide. According to Example 477 of U.S. Pat. No. 3,939,178, etodolac ethyl ester is produced by the reaction of 7-ethyltryptophol and the keto ester, ethyl propionyl acetate, using benzene as a solvent and p-toluenesulfonic acid as the catalysts. The product so obtained is purified by column chromatography, which is hydrolysed under alkaline conditions to give etodolac.

U.S. Pat. No. 4,585,877 discloses reaction of the methyl ester of 3-methoxy-2-pentenoic acid with 7-ethyltriptophol using dichloromethane as a solvent and boron trifluoride ethereate as the catalyst.

The methods described in the prior art suffer from several disadvantages:

Firstly, the use of strong acid catalysts exposes the desired product to other acid catalysed reactions resulting in the formation of impurities. In order to minimise the impurities, the ester is either purified by column chromatography before hydrolysis or the hydrolyzed product is purified at the cost of the yields and overall efficiency of the process. Moreover, the purification by column chromatography is very cumbersome and is disadvantageous at a commercial scale because of its efficiency and higher manufacturing costs.

Secondly, the use of carcinogenic solvents like benzene, tetrahydrofuran and strong acids like p-toluenefonic acid, boron trifluoride ethereate or sulfuric acid at industrial scale involves health hazards and poses serious environmental problems.

For purposes of patient safety, it is highly desirable to limit the amount of residual solvent present in any medicament administered to a patient. With this objective in mind, International Regulatory bodies impose stringent limits on residual solvents and categorize solvents in various classes depending upon their toxicity. The solvents used in prior art have been categorized in Class I category, which are highly toxic.

Therefore, the aim of the present invention is to provide an efficient process for the preparation of the esters of 1,8-disubstituted - 1,3,4,9-tetrahydropyrano (3, 4,6)- indole-1-acetic acid of formula I (as shown in the accompanied drawings), which process avoids the use of corrosive solvents, strong corrosive acids and gives a product of high purity and yield.

In general, molar equivalent proportions of 7-alkyltryptophol and B-ketoester is used. More preferably, 0.9–1.2 molar ratio of B-keto ester with respect to 7-alkyltriptophol is used but varying amounts of molar ratios are within the scope of this invention.

SUMMARY OF THE INVENTION

The present invention provides a process for the preparation of the esters of 1, 8-disubstituted-1,3,4,9-tetrahydropyrane (3,4-b)-indole-1 -acetic acid of Formula I:

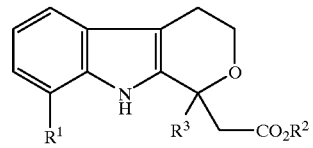

wherein $R_1$, $R_2$ and $R_3$ have the meanings as defined above, said process comprising reacting 7-alkyltryptophol of Formula II:

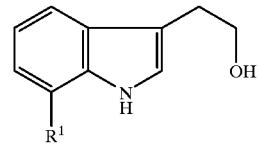

with a β-ketoester of the Formula III:

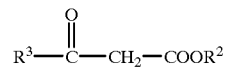

in a hydroxylic solvent, comprising at least one alkanol solvent having 1–4 carbon atoms, containing hydrogen chloride gas, and subsequently recovering the product of Formula I.

The term hydroxylic solvent means any lower alkanol and includes those primary secondary and tertiary alcohols. Suitable lower alkanol solvents include metanol, ethanol, n-propanol, isopropanol, n-butanol, isobutanol and t-butanol. Preferably, methanol is used as a solvent. Mixture of two or more lower alkanols can also be used.

The concentration of hydrogen chloride gas may range from 1% w/v to 20% w/v. However, a range of 5% to 15% w/v is generally preferred. The amount of solvent is at least 1 part by volume per part of the starting material, 7-substituted tryptophol. Higher amounts of solvents and generally upto 20 parts by volume can be used. However, a range of 5–10 parts by volume is generally preferred. Amounts higher than 20 parts are not useful from an economic point of view because large size reactor would be required.

Generally, the reaction is carried out in a temperature range from about −20° C. to the boiling point of the reaction mixture. The preferred temperature range is between about 0° C. to about 30° C. Persons skilled in the art will appreciate that the temperature range is given as a guide and may vary with the choice of solvent.

The reaction is typically accomplished within about 3–8 hours. However, the length of time required for reaction may vary depending on such factors as temperature of the reaction, volume of reaction mixture and size of batch and container and presence or absence of stirring.

In general, the reaction product directly crystallizes out of the reaction medium and is recovered by filtration to get substantially pure product of Formula I. Methods known in the art may be used with the process of this invention to enhance any aspect of this process. For example, the reaction mixture may be extracted with a solvent such as pentane or hexane. Such a solvent has the characteristic that the desired product is soluble in it and it does not form a homogeneous mixture with a hydroxylic solvent and the solvent is then removed to get the desired product. The product so obtained is hydrolysed by using methods known in the art to get the corresponding acid, e.g. etodolac.

DETAILED DESCRIPTION OF THE INVENTION

The present invention is illustrated by, but is by no means limited to, the following examples:

EXAMPLE 1

Preparation of Methyl 1,8-diethyl-1,3,4,9-tetrahydropropyrano(3,4-b)-indole-1-acetate To a solution of 7-ethyltryptophol (12.0 g) in methanolic hydrogen chloride (5% w/v, 100.0 ml), methyl 3-oxopentanoate (9.1 g) was added in one lot, at 25° C. The reaction mixture was stirred at 25–30° C. for 7 hours. The reaction mixture was then cooled to 0° C., and stirred at 0–5° C. for 3 hours. The product was filtered, washed with methanol and dried to afford the title compound (16.7 g, 89%), m.p. 128–130° C.; purity: 99.7%.

EXAMPLE 2

Preparation of Methyl 8-methyl-1-n-propyl-1,3,4,9-tetrahydropyrano (3,4-b)-indole-1-acetate To a solution of 7-methyltryptophol (10.0 g) in methanolic hydrogen chloride (5% w/v, 100.0 ml), methyl 3-oxohexanoate (9.1 g) was added in one lot, at 25° C. The reaction mixture was stirred at 25–30° C. for 7 hours. The reaction mixture was extracted with hexane (100.0 ml). Hexane was concentrated to about 20 ml and methanol (10 ml) was added. The mixture was stirred at 5–10° C. for 2 hours. The product was filtered, washed with methanol, and dried to afford the title compound (13.7 g, 80%); purity: 98.1%.

EXAMPLE 3

Preparation of Methyl 1,8-diethyl-1,3,4,9-tetrahydropyrano (3,4-b)-indole-1-acetate To a solution of 7-ethyltryptophol (12.0 g) in 1-butanolic hydrogen chloride (5% w/v, 100.0 ml), methyl 3-oxopentanoate (9.1 g) was added in one lot, at 25° C. The reaction mixture was stirred at 25–30° C. for 7 hours. The reaction mixture was extracted with hexane (100.0 ml). Hexane was concentrated to about 20 ml and methanol (10 ml) was added. The product was filtered, washed with methanol and dried to afford the titled compound (14.7 g, 79%), m.p. 128–130° C.; purity: 96.2%.

EXAMPLE 4

Preparation of Methyl 1,8-diethyl-1,3,4,9-tetrahydropyrano(3,4-b)-indole-1-acetate To a solution of 7-ethyltryptophol (12.0 g) in a mixture of methanolic hydrogen chloride (10% w/v, 50.0 ml) and toluene (50 ml), methyl 3-oxopentanoate (9.1 g, 0.07 mole) was added in one lot, at 25° C. The reaction mixture was stirred at 25–30° c for 7 hours. The reaction mixture concentrated to about 20 ml under reduced pressure. Methanol (50 ml) was added to the concentrate and the solution was extracted with hexane (100 ml). Hexane was concentrated to about 20 ml and methanol (10 ml) was added. The product was filtered, washed with methanol and dried to afford the title compound (15.8 g, 84%), m.p. 128–130° C., purity: 97.8%.

While the present invention has been described in terms of its specific embodiments, certain modifications and equivalents will be apparent to those skilled in the art and are intended to be included within the scope of the present invention.

We claim:

1. A process for the preparation of the ester of 1,8-disubstituted 1,3,4,9-tetrahydropyrano(3,4-b)-indole-1-acetic acid of Formula I:

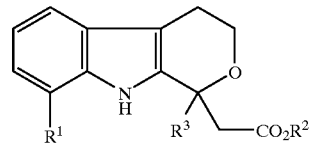

wherein $R_1$ is selected from the group consisting of hydrogen, lower alkyl and lower alkenyl, $R_2$ is selected from the group consisting of lower alkyl and aralkyl, $R_3$ is selected from the group consisting of lower alkyl, lower alkenyl, lower cyclohexyl, phenyl and benzyl, said process comprising reacting 7-alkyltryptophol of Formula II:

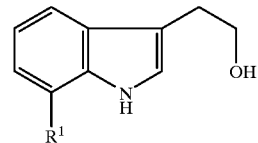

with a β-Ketoester of Formula III:

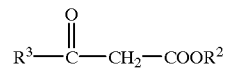

in a hydroxylic solvent, comprising at least one alkanol system having 1–4 carbon atoms, containing hydrogen chloride gas, and subsequently recovering the ester of Formula I.

2. The process of claim 1, wherein $R_2$ is lower alkyl in the compound of Formula I.

3. The process of claim 2, wherein $R_2$ is methyl in the compound of Formula I.

4. The process of claim 3, wherein $R_1$ is lower alkyl in the compound of Formula I.

5. The process of claim 4, wherein $R_1$ is ethyl in the compound of Formula I.

6. The process of claim 5, wherein $R_3$ is lower alkyl in the compound of Formula I.

7. The process of claim 6, wherein $R_3$ is ethyl in the compound of Formula I.

8. The process of claim 1 wherein the hydroxylic solvent comprises a lower alkanol.

9. The process of claim 1 wherein the hydroxylic solvent is methanol, ethanol, n-propanol, isopropanol, n-butanol, or t-butanol.

10. The process according to claim 1 wherein the concentration of hydrogen chloride gas in a hydroxylic solvent is 1–20% w/v.

11. The process according to claim 10 wherein the concentration of hydrogen chloride gas in a hydroxylic solvent is 5–15% w/v.

12. The process according to claim 1 wherein the reaction temperature is in the range −20° C. to 80° C.

13. The process according to claim 12 wherein the reaction temperature is in the range 0° C. to 30° C.

14. The process of claim 1 wherein said hydroxylic solvent contains hydrogen chloride gas at the time said reactants are dissolved therein.

15. The process of claim 1 wherein said hydrogen chloride gas is added to the reaction mixture after said reactants are dissolved in said hydroxylic solvent.

16. The process of claim 1 wherein the esters of 1,8-disubstituted 1,3,4,9-tetrahydropyrano(3,4-b)-indole-1-acetic acid of Formula I are recovered by filtration.

17. The process of claim 1 wherein the ester of 1,8-disubstituted 1,3,4,9-tetrahydropyrano(3,4-b)-indole-1-acetic acid of Formula I are recovered by extracting the reaction mixture with a solvent, wherein said solvent has the characteristic that the ester of Formula I is soluble in it and it does not form a homogeneous mixture with said hydroxylic solvent, and subsequently recovering the ester of Formula I by removing the solvent.

18. The process of claim 17 wherein said solvent is selected from pentane and hexane.

* * * * *